US00PP13368P2

(12) United States Plant Patent

Olesen et al.

(10) Patent No.: US PP13,368 P2

(45) Date of Patent: Dec. 17, 2002

(54) MINIATURE ROSE PLANT NAMED 'POULRAV'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/277,240

(22) Filed: Mar. 26, 1999

(51) Int. Cl.[7] ..... A01H 5/00

(52) U.S. Cl. ..... Plt./116

(58) Field of Search ..... Plt./116, 119, 118

(56) References Cited

U.S. PATENT DOCUMENTS

PP6,810 P * 5/1989 Meilland ..... Plt./118
PP8,001 P * 10/1992 McGredy, IV ..... Plt./139
PP8,011 P * 10/1992 Olesen et al. ..... Plt./118

OTHER PUBLICATIONS

Canadian Food Inspection Agency "Applications Accepted for Filing" Jul. 1998 Canada 1 Page.

Community Plant Variety Office "Certificate on the Grant . . . " Oct 2, 2000 8 pages. EU.

Community Plant Variety Office "UPOV Extract" EU 3 Pages.

Community Plant Variety Office "Proposal for Variety Denomination" Aug. 14, 1995 EU 1 page. (In Danish).

Research Center for Cultivar Testing "Decision" Feb. 22, 1999 Poland 1 Page.

Ministry of Agriculture and Rural Development "Notice on the Grant of Plant Breeders Rights" Aug. 15, 1999. Poland. 1 page.

UPOV–ROM, 2001/01, Plant Variety Database, GTI Jouve Retrieval Software, citation for 'POULtrav'.*

Haring, ed., 1986, Modern Roses 9, The American Rose Society, Shreveport, Louisiana, p. 326.*

UPOV–ROM, 2000/05, Plant Variety Database, GTI Jouve Retrieval Software, citation for 'POULrav'.*

* cited by examiner

*Primary Examiner*—Howard J. Locker

(57) ABSTRACT

A new garden rose plant which has abundant, amber yellow flowers and attractive, disease resistant foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between 'MEIponal' (U.S. Plant Pat. No. 6,810, issued on May 23, 1989), and an unnamed non-commercial seedling. The two parents were crossed and the resulting seeds were planted in a controlled environment. The new variety is named 'POULtrav'.

The new rose may be distinguished from its seed parent, 'MEIponal', by the following combination of characteristics:

1. The seed parent is patio rose with bright yellow-orange blooms.

2. The seed parent has approximately 35 petals per flower; whereas, 'POULtrav' has 38–44 petals per flower;

3. The seed parent is without fragrance; whereas, the fragrance of 'POULtrav' is described as a moderate fruity fragrance.

The new variety may be distinguished from its pollen parent, unnamed seedling created by the same inventors, by the following combination of characteristics:

1. The pollen parent has soft yellow blooms compared to the amber blooms of 'POULtrav'.

2. The pollen parent is smaller in height and width compared to 'POULtrav'.

The objective of the hybridization of this rose variety garden use was to create a new and distinct variety with unique qualities, such as:

1. Uniform and abundant flowers;
2. Vigorous, compact growth;
3. Amber yellow blooms;
4. Disease resistance.

This combination of qualities is not present in previously available commercial cultivars of this type and distinguishes 'POULtrav' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULtrav' was selected in the spring, 1989 by the inventors as a single plant from the progeny of the aforementioned hybridization. Asexual reproduction of 'POULtrav' by cuttings and traditional budding was first done by L. Pernille and Mogens N. Olesen in August, 1989, at their nursery in Fredensborg, Denmark. This initial and other subsequent propagations conducted in controlled environments have demonstrated that the characteristics of 'POULtrav' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems of 'POULtrav'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULtrav', as observed in its outdoor growth in a field nursery in Jackson County, Oreg. Observations were conducted during September, 1998. Color references are made using The Royal Horticultural Society (London, England) Colour Chart, 1995, except where common terms of color are used.

For a comparison, several physical characteristics of the rose variety 'POULwee', a miniature rose variety from the same inventors described and illustrated in U.S. Plant Pat. No. 8,011 and issued on Oct. 27, 1992 are compared to 'POULtrav' in Chart 1.

CHART 1

| | 'POULtrav' | 'POULwee' |
|---|---|---|
| Size of open bloom. | 40 mm. | 35–40 mm. |
| Petalage. | Very Double, 38–44 petals. | Double, 26–28 petals. |
| Petal color, upper surface, after opening. | Red Group 34C–36C for marginal zone and Yellow-Orange Group 14C & 23B for middle zone. | Yellow Group 12A to Yellow-Orange Group 14B. |

Parents:

*Seed parent.*—'MEIponal'.

*Pollen parent.*—Unnamed seedling.

Classification:

*Botanical.*—*Rosa hybrida.*

*Commercial.*—Miniature.

FLOWER AND FLOWER BUD

Blooming habit: Continuous.

Flower bud:

*Size.*—Upon opening, 20 mm–25 mm in length from base of receptacle to end of bud.

*Bud form.*—Pointed ovoid.

*Bud color.*—As sepals unfold, a blend of Orange Group 24C and Red Group 51C. Yellow-Orange Group 19A at ¼ opening.

*Sepals.*—Green Group 144A. Moderate foliaceous appendages on four of the five sepals. Interior surface of sepals are moderately pubescent. A limited number of stipitate glands are located along the margins of the sepals.

*Receptacle.*—Surface: Smooth. Shape: Funnel-shaped. Size: Small, 7 mm (h)×4 mm (w). Color: Green Group 144B.

*Peduncle.*—Surface: Covered with a moderate number of fine prickles and stipitate glands. Length: 15–20 mm average length. Color: Green Group 144A, with anthocyanin coloration Greyed-Purple 183B. Strength: Erect.

*Borne.*—Multiple buds per stem; 1–6 buds per flowering stem.

Flower bloom:

*Fragrance.*—Moderate fruity-fresh scent.

*Duration.*—As a cut flower 3 to 6 days. The blooms have a duration on the plant of approximately 5 to 7 days. Petals fall cleanly away from plant.

*Size.*—Average flower diameter is 40 mm when open.

*Form.*—Shape of flower when viewed from the side: Upon opening, upper part: Flattened convex. Upon opening, lower part: Flat. Open flower, upper part: Flat. Open flower, lower part: Flattened convex.

*Petalage.*—Very double; 38–44 petals under normal conditions with 4–8 petaloids.

Color:

*Upon opening, petals.*—Outermost petals: Upper Surface: Orange Group 26C. Reverse Side: Outer margin of petal Orange Group 26B. Center of petal has tone of Red Group 37B. Innermost petals: Upper Surface: Orange Group 26A. Reverse Side: Orange Group 25C.

*Upon opening, basal petal spots.*—Outermost petals: Outer Side: Green-Yellow Group 1B. Inner Side: Green-Yellow Group 1C. Innermost petals: Outer Side: Green-Yellow Group 1A. Inner Side: Green-Yellow Group 1B.

*After opening, petals.*—Close examination of petals shows very uneven coloring. There is a deep Yellow undertone of Yellow Group 13A overlaid with a Orange blush in the tone Orange Group 24A. As flower opens the outer petals under fades into a Pink to pastel Orange (Orange Group 27C to Red Group 36D) and the blush is more in the tone of Red Group 37C. The middle and basal zones continue to hold a yellow tone.

*Outermost petals.*—Upper Surface: Marginal zone Red Group 34C and Red Group 36C. Middle zone Yellow-Orange Group 14C and Yellow-Orange Group 23B. Reverse Side: Marginal zone Red Group 36C. Middle zone Yellow Group 13C.

*Innermost petals.*—Upper Surface: Yellow-Orange Group 23B. Reverse Side: Yellow-Orange Group 23B.

*After opening, basal petal spots.*—Outermost petals: Outer Side: Yellow Group 9B. Inner Side: Yellow Group 9A. Innermost petals: Outer Side: Yellow Group 13A. Inner Side: Yellow Group 13A.

General tonality: On open flower Orange Group 24B. No change in the general tonality at the end of the 4th day. Afterwards, general tonality is a blend Orange Group 27C and Orange Group 25C.

Petals:

*Petal reflex.*—Moderate to strongly reflexed.

*Petal edge.*—Uniform.

*Shape.*—Deltoid shaped.

*Petaloids.*—4–8 petaloids.

*Texture.*—Thin, soft petals.

*Arrangement.*—Informal.

Reproductive organs:

*Pollen.*—Color: Orange Group 26A. Quantity: Average.

*Anthers.*—Size: Medium. Color: Immature: Yellow-Orange Group 20B. Mature: Yellow-Orange Group 15B.

*Filaments.*—Color: Yellow Group 12A.

*Stigmas.*—Slightly superior in location to anthers. Color: Yellow Group 2B.

*Styles.*—Color: Yellow-Green Group 149C. Intonations: Red striation on some of the styles in tone of Red Group 50A–50B.

*Hips.*—None observed.

PLANT

Plant growth: Moderate, bushy. When grown as a budded field grown plant on *Rosa multiflora* understock, the average height of the plant itself is 40 cm and the average width is 40 cm.

Stems:

*Color.*—Young wood: Yellow-Green Group 144A. Older wood: Yellow-Green Group 144A.

*Thorns.*—Incidence: Few thorns. Size: Average length: 5–6 mm. Color: Base of thorn Greyed-Red Group 179C with tip of thorn Yellow-Green Group 144C. Shape: Concave.

*Surface.*—Young wood: Smooth. Older wood: Smooth.

Plant foliage: Normal number of leaflets on leaves in middle of the stems: 5 leaflets.

*Leaf size.*—Small, 50 mm (l)×35 mm (w).

*Quantity.*—Average.

*Color.*—Upper Leaf Surface: Green Group 137A. Lower Leaf Surface: Yellow-Green Group 146C. Juvenile foliage: Upper leaf surface is Yellow-Green Group 146A. Lower leaf surface is Green Group 138B. Anthocyanin: Location: Lower leaflet surfaces, leaflet margin, leaf, rachis, petiole and stem. Anthocyanin typically lasts for 3 to 4 weeks. Color: Greyed-Red Group 180A.

Plant leaves and leaflets:

*Stipules.*—Size: 8 mm–10 mm. Color: Green Group 137A. Stipitate glands: On margins of stipules.

*Petiole.*—Length: 14 mm–16 mm. Color: Green Group 137B. Underneath: Smooth, with occasional small prickle in petiole region. Margins: With limited numbers of stipitate glands.

*Rachis.*—Color: Green Group 137B. Underneath: Smooth with occasional small prickle. Margins: Limited number of stipitate glands.

*Leaflet.*—Edge: Finely serrated. Shape: Ovate. Texture: Thin leaflets with matte finish.

Disease resistance: Above average resistance to mildew, rust and black spot under normal growing conditions in Jackson County, Oreg.

Cold hardiness: 'POULtrav' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant, amber yellow flowers, vigorous growth, disease resistance, and extended period of bloom.

* * * * *

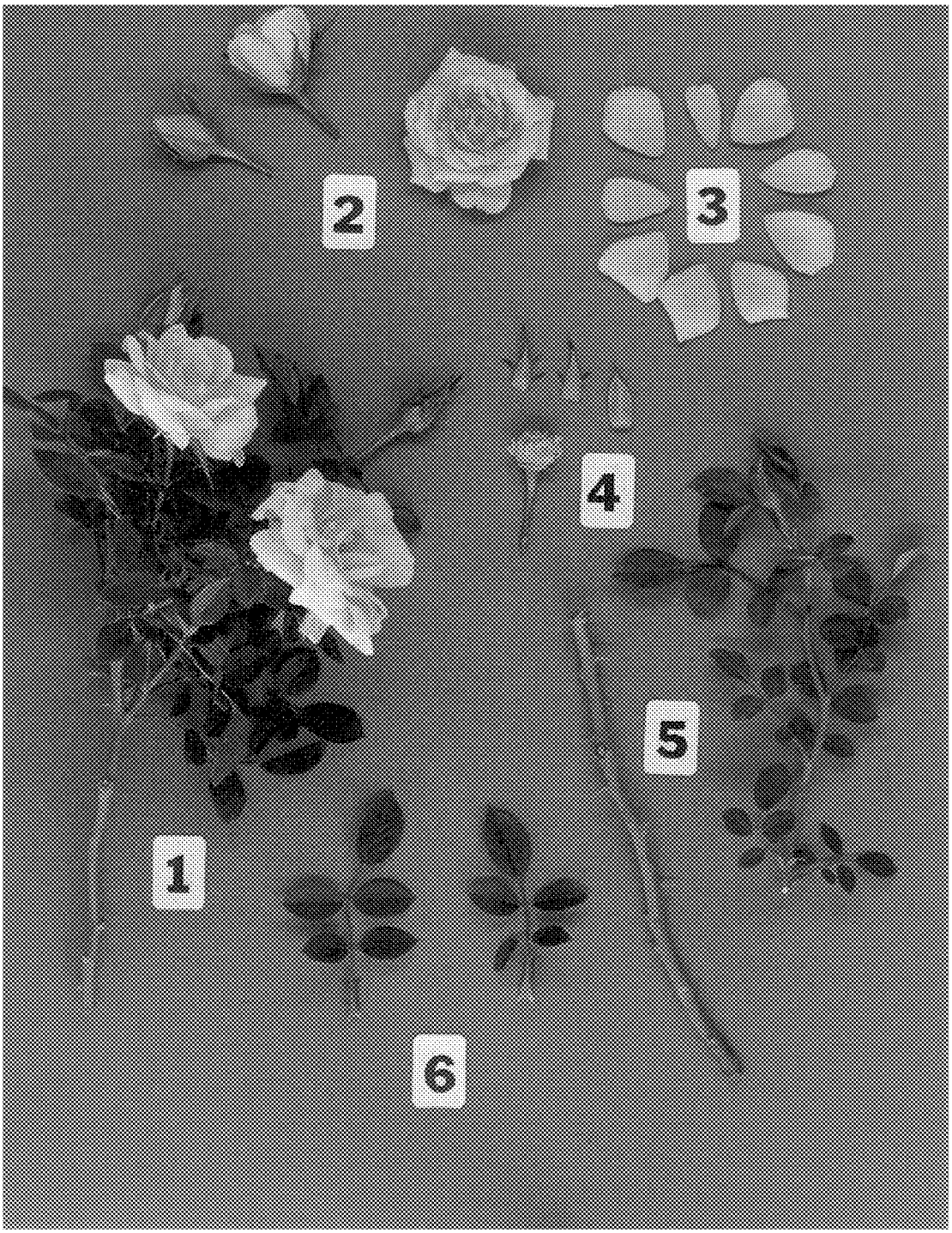
2
3
4
5
1
6